(12) United States Patent
Ignacio et al.

(10) Patent No.: US 6,440,744 B1
(45) Date of Patent: *Aug. 27, 2002

(54) STERILIZATION MONITORING METHOD

(75) Inventors: Ramon T. Ignacio, Somerville; Allan P. Piechowski, Califon, both of NJ (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,859

(22) Filed: Jan. 5, 2000

Related U.S. Application Data

(60) Division of application No. 09/019,341, filed on Feb. 5, 1998, now Pat. No. 6,287,518, which is a continuation-in-part of application No. 08/882,630, filed on Jun. 25, 1997, now abandoned.

(51) Int. Cl.$^7$ ................................................. A61L 2/28
(52) U.S. Cl. ............................ 436/1; 436/169; 422/28; 422/37
(58) Field of Search .......................... 422/86, 5, 6, 28, 422/87, 37, 12; 436/1, 164, 169

(56) References Cited

U.S. PATENT DOCUMENTS

| | | | |
|---|---|---|---|
| 3,098,751 A | 7/1963 | Huyck et al. | 106/20 |
| 3,183,173 A | 5/1965 | Oakes | 195/103.5 |
| 3,627,469 A | 12/1971 | Cheng | 23/232 |
| 3,627,698 A | 12/1971 | Rey et al. | 252/408 |
| 3,654,179 A | 4/1972 | Bauer | 252/408 |
| 3,654,180 A | 4/1972 | Bauer | 252/408 |
| 3,667,916 A | 6/1972 | Sliva et al. | 23/230 R |
| 3,704,096 A | 11/1972 | Verses et al. | 23/230 R |
| 3,862,824 A | 1/1975 | Chapman | 23/253 |
| 3,899,295 A | 8/1975 | Halpern | 23/253 TP |
| 4,042,336 A | 8/1977 | Larsson | 23/253 TP |

(List continued on next page.)

FOREIGN PATENT DOCUMENTS

| | | |
|---|---|---|
| DE | 2 027 604 | 5/1970 |
| DE | 268 396 A1 | 5/1989 |
| DE | 273 776 A1 | 11/1989 |
| DE | 90 04 818 | 4/1990 |
| EP | 0 014 447 A1 | 8/1980 |
| EP | 0 069 037 A1 | 1/1983 |
| EP | 0 421 760 B1 | 3/1994 |
| EP | 0 707 186 A1 | 4/1996 |
| EP | 914 833 | 5/1999 |
| JP | Sho. 49-46440 | 12/1974 |
| WO | WO93/16386 | 8/1993 |
| WO | WO95/06134 | 3/1995 |
| WO | WO 96/33242 | 10/1996 |
| WO | WO 98/46994 | 10/1998 |

OTHER PUBLICATIONS

Indicators based on phenol red and magnesium bromide, and their use in hydrogen peroxide sterilization device.
Indicators based on phenol red and magnesium bromide, and their use in peracetic acid sterilization device.

(List continued on next page.)

Primary Examiner—Jeffrey Snay
(74) Attorney, Agent, or Firm—John A. Burtis

(57) ABSTRACT

A sterilization monitor includes a substrate and an monitor composition. The monitor composition contains a colorant and a halogen source and undergoes a distinct color change when exposed to a peracid. The sterilization monitor can be used to monitor a sterilization process involving a peracid. A sterilization monitoring device, including a sterilization monitor enclosed in a housing having a vapor permeable barrier, can also be used to monitor a sterilization process.

18 Claims, 1 Drawing Sheet

U.S. PATENT DOCUMENTS

| | | | | |
|---|---|---|---|---|
| 4,091,921 | A | 5/1978 | Lewis | 206/363 |
| 4,098,577 | A | 7/1978 | Halpern | 23/232 R |
| 4,138,216 | A | 2/1979 | Larsson et al. | 422/56 |
| 4,145,186 | A | 3/1979 | Andersen | 23/232 R |
| 4,155,895 | A | 5/1979 | Rohowetz et al. | 260/33.4 |
| 4,165,399 | A | 8/1979 | Germonprez | 427/264 |
| 4,166,044 | A | 8/1979 | Germonprez et al. | 252/408 |
| 4,168,779 | A | 9/1979 | Yokokoji et al. | 206/439 |
| 4,179,397 | A | 12/1979 | Rohowetz et al. | 252/408 |
| 4,188,437 | A | 2/1980 | Rohowetz | 428/199 |
| 4,206,844 | A | 6/1980 | Thukamoto et al. | 206/439 |
| 4,240,926 | A | 12/1980 | McNeely | 252/408 |
| 4,314,344 | A | 2/1982 | Johns et al. | 364/500 |
| 4,328,182 | A | 5/1982 | Blake | 422/56 |
| 4,407,960 | A | 10/1983 | Tratnyek | 436/1 |
| 4,416,984 | A | 11/1983 | Wheeler, Jr. | 435/31 |
| 4,448,548 | A | 5/1984 | Foley | 374/160 |
| 4,461,837 | A | 7/1984 | Karle et al. | 435/296 |
| 4,521,376 | A | 6/1985 | Witonsky et al. | 422/56 |
| 4,579,823 | A | 4/1986 | Ryder | 435/296 |
| 4,596,773 | A | 6/1986 | Wheeler, Jr. | 435/31 |
| 4,643,876 | A | 2/1987 | Jacobs et al. | 422/23 |
| 4,671,936 | A | 6/1987 | Barron | 422/55 |
| 4,673,635 | A | 6/1987 | Yamanishi et al. | 435/10 |
| 4,717,661 | A | 1/1988 | McCormick et al. | 435/31 |
| 4,741,437 | A | 5/1988 | Gorski et al. | 206/222 |
| 4,756,758 | A | 7/1988 | Lent et al. | 106/22 |
| 4,756,882 | A | 7/1988 | Jacobs et al. | 422/23 |
| 4,828,797 | A | 5/1989 | Zwarun et al. | 422/55 |
| 4,839,291 | A | 6/1989 | Welsh et al. | 435/296 |
| 4,885,253 | A | 12/1989 | Kralovic | 435/296 |
| 4,898,762 | A | 2/1990 | Brown et al. | 428/152 |
| 4,935,371 | A | 6/1990 | Rickloff | 435/296 |
| 5,073,488 | A | 12/1991 | Matner et al. | 435/31 |
| 5,084,239 | A | 1/1992 | Moulton et al. | 422/22 |
| 5,087,659 | A | 2/1992 | Fujisawa | 524/594 |
| 5,139,957 | A | 8/1992 | Grack | 436/135 |
| 5,167,923 | A | 12/1992 | Van Iperen | 422/58 |
| 5,254,473 | A * | 10/1993 | Patel | 436/1 |
| 5,260,023 | A | 11/1993 | Evans, II | 422/40 |
| 5,316,575 | A | 5/1994 | Lent et al. | 106/20 |
| 5,344,017 | A | 9/1994 | Wittrock | 206/459.1 |
| 5,377,496 | A | 1/1995 | Otto et al. | 62/129 |
| 5,389,336 | A | 2/1995 | Childers | 422/28 |
| 5,451,372 | A | 9/1995 | Larsson et al. | 422/58 |
| 5,482,684 | A * | 1/1996 | Martens et al. | 422/119 |
| 5,498,526 | A | 3/1996 | Caputo et al. | 435/31 |
| 5,516,648 | A | 5/1996 | Malchesky et al. | 435/31 |
| 5,518,927 | A | 5/1996 | Malchesky et al. | 436/1 |
| 5,552,320 | A | 9/1996 | Smith | 435/287.4 |
| 5,620,656 | A * | 4/1997 | Wensky et al. | 422/28 |
| 5,623,810 | A | 4/1997 | Dey et al. | 53/425 |
| 5,709,067 | A | 1/1998 | Dey et al. | 53/430 |
| 5,732,529 | A | 3/1998 | Dey et al. | 53/389.2 |
| 5,882,611 | A | 3/1999 | Williams et al. | 422/292 |
| 5,887,716 | A | 3/1999 | Williams et al. | 206/459.1 |
| 6,238,623 | B1 * | 5/2001 | Amhof et al. | 422/58 |

OTHER PUBLICATIONS

Indicators based on bromcresol purple and second blue dye, and their use in peracetic acid sterilization device.

Indicators based on ethyl red and a green pigment, and their use in peracetic acid sterilization device.

P. Mecke, "Hydrogen Peroxide Plasma—an Interesting Microbiocidal Concept", Hygiene Medizin, 1992, 17:537–543.

Gunter Spicher, "Biological Indicators and Monitoring Systems for Validation and Cycle Control of Sterilization Processes", Zbl. Bakt. hyg. A 267, 463–484, 1988.

Eskenazi et al., "Evaluation of Glutaraldehyde and Hydrogen Peroxide for Sanitizing Packaging Materials of Medical Devices in Sterility Testing", J. Assoc. Off. Anal. Chem. (vol. 65, No. 5) 1982.

Steris Process, Chemical Monitoring Strips for Independent Monitoring of the Steris Process, Brochure of Steris Corporation.

Indicators based on bromcresol purple and a green dye, and their use in peracetic acid sterilization device.

Indicators based on pinacyanol and an oil soluble orange colorant, and their use in peracetic acid sterilization device.

Indicators based on cobalt hydroxide and their use in peracetic acid sterilization device.

Indicators based on acid fuchsin and a green dye, and their use in peracetic acid sterilization device.

Indicators based on crystal violet lactone and a green dye, and their use in peracetic acid sterilization device.

Derwent Publications Ltd., JP 49 046440 B, Dec. 10, 1974 (abstract).

Alfa et al., "Comparison of Ion Plasma, Vaporized Hydrogen Peroxide, and 100% Ethylene Oxide Sterilizers to the Dec. 1988 Ethylene Oxide Gas Sterilizer", Infection Control and Hospital Epidemiology, pp. 92–100, Feb. 1996.

Steris Process Monitoring, 612025 Rev. C, May 1995.

Advertisements for Sterrard Chemical Indicator Strip, Advanced Sterilization Products, 1995.

Nancy C. Chobin, RN, "Cost analysis of three low–temperature sterilization systems", pp. 29–34, Journal of Healthcare Material Management, Aug. 1994.

John McCormack, "Ask these questions before buying new sterilization technologies," Materials Management, 68–69, Jun. 1994.

"Sterilization Using Gaseous Hydrogen Peroxide—Validation of the VHP™ Series 100 Endoscope Sterilizer for Sterilization of Rigid Endoscopes . . . ", Technical Report, Amsco International, Inc., Apr. 1994.

Borneff et al., On the Efficacy and Validation of $H_2O_2$ Plasma Sterilizers.

Derwent Abstract Accession No. 94–315093/39, class S03, SU 1817022 A (EREV IREA Inorg Materials Sect) Mar. 12, 1991.

* cited by examiner

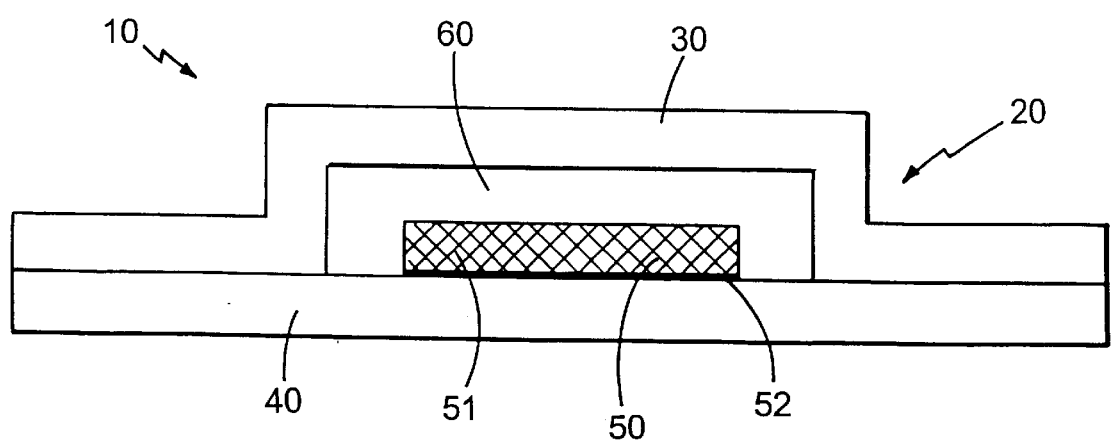

STERILIZATION MONITORING METHOD

This application is a divisional of U.S. Ser. No. 09/019,341, filed Feb. 05, 1998 now U.S. Pat. No. 6,287,518, which is a continuation-in-part of U.S. Ser. No. 08/882,630, filed Jun. 25, 1997, now abandoned.

BACKGROUND OF THE INVENTION

Medical instruments and parenteral drugs are sterilized prior to use. A traditional sterilization process uses steam under pressure. Alternative sterilization processes use ethylene oxide, hydrogen peroxide, or peracetic acid in the vapor form as the sterilant.

Sterilization processes using peracid solutions may be performed in a sterilization chamber. During a typical sterilization cycle, the instruments being sterilized are exposed to a sterilization solution containing, for example about 2000 ppm or 2500 ppm of peracetic acid. The instruments are exposed to the solution for a sufficient time at a sufficiently high enough temperature, e.g., 50° C.–60°C., for the sterilization to be effective.

SUMMARY OF THE INVENTION

The invention features monitoring a sterilization process that uses a vapor including a peracid (e.g., peracetic acid) with a monitor composition. The monitor composition contains a colorant and a halogen source. During the sterilization process, the peracid contacts the monitor composition, resulting in halogenation of the colorant to occur. Halogenation of the colorant causes the colorant and the monitor composition to undergo a distinct, permanent color change that provides an indication that sterilization has occurred. A distinct color change in the indicator composition occurs if normal medical professional can readily discern the color change through visual observation.

Preferred colorants include dyes such as the sodium salt of fluorescein or phenol red that is susceptible to halogenation.

The invention also features sterilization indicators including a substrate and the indicator composition, as well as the indicator composition itself. The indicator composition can be used, for example, on indicating labels, or indicator tapes, and in devices that monitor the variables of a sterilization process (e.g., time, temperature, and concentration).

In another aspect, the invention features a monitor composition for monitoring a sterilization process including peracid, e.g., peracetic acid. The monitoring composition contains a colorant and a halogen source. When the monitoring composition is exposed to the peracid during a sterilization process the peracid causes halogenation of the colorant, which causes the monitoring composition to undergo a color change. The halogenated colorant may in turn be susceptible to additional reactions which cause the monitoring composition to undergo a further distinct color change, dependent upon, e.g., the concentration of the peracid in the solution. The colorant may be a dye such as phenol red.

The invention also features a method of monitoring peracid liquid phase sterilization processes. The monitor composition-includes a colorant and is exposed to a solution including peracid during a sterilization process. The monitoring composition will change to a particular color if the sterilization process meets certain pre-determined sterilization parameters, such as exposure time, exposure temperature, and exposure concentration of peracid (e.g., 1 minute, 25° C., and 1000 ppm of peracid).

The invention also features a method of determining whether a solution including peracid has a concentration of peracetic acid of about 2500 ppm. The monitor composition is exposed to the peracetic acid solution under conditions that will cause the monitor composition to undergo a color change at about 2500 ppm of peracetic acid.

The invention also features a method of monitoring a sterilization process that uses a liquid peracid sterilant by contacting a sterilization monitoring device with a liquid peracid from a sterilization solution during the sterilization process. The sterilization monitoring device includes a vapor permeable barrier and a monitor composition. The peracid vapor from the liquid sterilant penetrates the vapor barrier contacting the monitor composition including a colorant susceptible to halogenation and a halogen source, and the peracid contacts the halogen source to produce halogen which halogenates the colorant to cause a color change in the composition.

The invention also features a sterilization monitoring device including a housing having a vapor permeable barrier and a monitor composition enclosed within the housing. The monitor composition includes a halogen source and a colorant susceptible to halogenation in the presence of a peracid from a sterilization solution. The peracid contacts the halogen source to produce halogen which halogenates the colorant to cause a color change in the composition.

The invention also features a sterilization monitoring device including a substrate, having a laminated side, carrying a monitoring composition, and a housing having a vapor permeable barrier. Preferably, the housing also includes a vapor impermeable barrier. The vapor impermeable barrier defines a vapor head space. The substrate is enclosed within the housing with the laminated side mounted to the vapor permeable barrier.

Other features and advantages of the invention will be apparent from the description of the preferred embodiment thereof, and from the claims.

BRIEF DESCRIPTION OF THE DRAWINGS

The FIGURE is a cross-sectional view of a sterilization monitoring device.

DESCRIPTION OF THE PREFERRED EMBODIMENTS

Sterilization monitors and sterilization monitoring devices are used to monitor sterilization processes that include the use of a peracid. The sterilization monitors and monitoring devices also can be used to determine the concentration of a peracid present during the sterilization process.

The peracid may be any of the conventional peracids known to be useful as sterilants. The peracids may contain, for example, between one and eight carbon atoms, may be saturated or unsaturated, may be halogenated, and may be aliphatic, aromatic, or non-aromatic. Examples include performic acid, peracetic acid, perpropinoic acid, perbutanoic acid, etc.

Examples of Sterilization Monitors for Vapor Phase Sterilization Processes

A preferred sterilization monitor for vapor phase sterilization processes includes a monitor composition and a substrate.

The monitor composition undergoes a distinct color change when exposed to peracid vapor. For example, the monitor composition, carried on the substrate, may exhibit the distinct color change within a certain period of time (e.g., 5 minutes, 15 minutes, or 2 hours) of exposure to an atmosphere containing 5% peracetic acid at room temperature. The color of the monitor composition (prior to or after exposure to peracetic acid) preferably does not change or fade if left exposed to normal fluorescent lights at a distance of three inches for one or two days.

A preferred monitor composition contains a dye, a halogen source, and a binder resin.

The dye is susceptible to halogenation in the presence of a halogen source and a peracid, and changes color as a result of the halogenation to provide a distinct color change in the monitor composition. Once halogenation is complete the color of the dye does not change if left exposed to normal air. As a result, assuming the dye is the only colorant in the monitor composition, once halogenation of the dye is complete the color of the monitor composition is essentially fixed. Examples of such dyes include the sodium salt of fluorescein (acid yellow 73) and phenol red. A monitor composition containing fluorescein (acid yellow 73), for instance, in the presence of a bromine source and a peracid, will turn from yellow to orange, and in the presence of an iodine source will turn from yellow to red.

A sufficient quantity of the dye should be included in the monitor composition to provide the desired color intensity. The quantity of the dye in the composition also will influence the rate at which the composition undergoes the distinct color change. The indicator composition may contain, for example, between 0.5% and 10%, or between 1% and 5%, of the dye by weight.

The halogen source can be, for example, a halogen salt, such as alkaline earth metal halide salts (e.g., magnesium bromide or magnesium iodide) or alkali metal halide salts (e.g., potassium bromide). A sufficient quantity of the halogen source should be included in the monitor composition to react with a sufficient quantity of the dye to cause the color change at the desired rate. The monitor composition may contain, for example, between 1% and 60%, or 5% and 45%, of the bromine source by weight.

The binder resin binds the composition to the substrate. Examples of binder resins include shellac, ethyl cellulose, hydroxypropyl methylcellulose, methyl cellulose, and ethyl hydroxyethyl ethylcellulose. The shellac can be, for example, bleached bone dry shellac. A sufficient quantity of binder resin should be included in the composition to provide adequate binding of the composition to the substrate. The binder resin also may influence the rate at which peracid penetrates into the composition during the sterilization process. The rate of peracid penetration, in turn, may influence the rate of color change of the composition. The monitor composition may contain, for example, between 20% and 98%, or between 40% and 70%, of the resin binder by weight.

The monitor composition optionally may include other ingredients such as colorants that do not change color during the sterilization process, resins that perform functions other than binding (e.g., providing water resistance or solvent dispersibility), or opacifying agents.

Prior to application to the substrate, the monitor composition is dissolved/dispersed in a suitable solvent (e.g., water or a lower-alkyl ($C_1$–$C_4$) alcohol like ethanol or isopropyl). Generally, anywhere from one to two parts of solvent to one part of the indicator composition may be used.

The substrate may be, for example, blotter paper, which typically has a neutral pH, polyester (e.g., Melinex Polyester film or crepe paper). The substrate may be in the form of a strips, having the indicator composition at one end; the other end can serve as a grip for the user. When the substrate is an absorbent material such as blotter paper, the grip portion of the strip may be laminated with a plastic outer surface to minimize the absorption of peracid or other sterilization components by the grip during the sterilization process.

The substrate may also have an adhesive on the bottom surface that allows the sterilization monitor to be used as a label or as tape. An example of a suitable polyester label is Copycode WH®, a white polyester with a printable topcoat manufactured by the Fasson Film Division of Avery-Dennison Co. A suitable masking tape includes crepe paper from Endura Products on an upper surface to carry the monitor composition.

The monitor composition may be applied to the substrate by any suitable technique. For example, the indicator composition may be applied to the substrate using dip coating or conventional printing techniques such as flexographic printing, extrusion printing, or gravure printing.

Examples 1 and 2 are examples of vapor phase sterilization monitors.

EXAMPLE 1

A monitor composition (in solvent) was prepared that contained the following ingredients:

| Ingredient | Quantity | Supplier |
| --- | --- | --- |
| Acid Yellow 073 | 3 Grams | Spectra Dyes |
| Isopropyl Alcohol | 50 Grams | — |
| Shellac Bleached Bone Dry (V-117) | 50 Grams | Zehrung Corp. |
| Ethanol | 50 Grams | — |
| Magnesium bromide | 30 Grams | Aldrich |

The composition was prepared according to the following procedure. The shellac bleached bone dry is weighed into a 500 ml disposable plastic beaker. The ethyl alcohol is weighed into a separate 500 ml disposable plastic beaker. The beaker containing ethyl alcohol is placed under a disperser. While the disperser runs at a slow speed, the shellac bleached bone dry is added slowly to the beaker. Stirring continues until the resin has completely dissolved.

The isopropyl alcohol is weighed into a 100 ml beaker, and transferred to a #00 mill jar. The sodium salt of fluoroscein (acid yellow 73) is weighed into an aluminum pan, and also transferred to the #00 mill jar. In addition, the magnesium bromide is weighed into a 100 ml disposable beaker, and transferred to #00 mill jar. The ethanol solution then also is transferred to #00 mill jar and the mixture is ground for four hours to provide the indicator composition (in solution).

Swatches are made with indicator composition on blotter paper using an Acculab Jr. drawdown machine with #0 rod. A strip (approximately 3"×½") was cut from the blotter paper, and hung inside a bottle containing 5% peracetic acid and 22% hydrogen peroxide. The monitor composition initially is yellow, but the color changes to red within 10 minutes as the peracetic acid contacts the indicator composition and causes the bromination of the acid yellow 73.

EXAMPLE 2

A monitor composition (in solvent) containing phenol red was prepared that contained the following ingredients:

| Ingredient | Quantity | Supplier |
|---|---|---|
| Ethyl Alcohol | 1000.00 grams (54.34%) | — |
| Phenol Red | 20.00 grams ( 1.09%) | Aldrich |
| Magnesium Bromide | 200.00 grams (10.87%) | — |
| V-129* | 600.00 grams (32.61%) | — |
| Shellac Bleached Bone Dry (V-117) | 20.00 grams ( 1.09%) | Zehrung Corp. |

*V-129 includes 9.3 grams of Methocel 50 CPS (from Dow Chemical), 9.3 grams of Methocel 4,000 CPS (from Dow Chemical), 348.84 grams of distilled water, and 232.56 grams of ethyl alcohol.

The composition was prepared and tested according to the following procedure. The phenol red is weighed into a 100 ml disposable plastic beaker, and transferred to #00 mill jar. The magnesium bromide is weighed into a 250 ml disposable plastic beaker, and also transferred to the #00 mill jar. The V-129 is weighed into a in 1000 ml disposable plastic beaker, and transferred to the #00 mill jar. In addition, the V-117 is weighed into a 100 ml disposable plastic beaker, and transferred to the #00 mill jar. Finally, the isopropyl alcohol is weighed into a 100 ml beaker, and also transferred to the #00 mill jar.

The mixture is ground in the mill jar for one hour to provide the monitor composition (in solution). Swatches of the monitor composition are made on blotter paper and on Kimdura synthetic paper using the Acculab Jr. drawdown machine with #0 rod. Strips (about 3"×½") are cut and hung inside the bottle containing 5% peracetic acid and 22% hydrogen peroxide.

The monitor composition printed on Kimdura synthetic paper initially was yellow, but it turned from yellow to blue within 20 minutes at room temperature as the peracetic acid contacted the monitor composition and caused the bromination of the phenol red. The monitor composition printed on blotter paper also initially was yellow. It turned from yellow to green in 10 minutes at room temperature as the peracetic acid contacted the monitor composition and caused the bromination of the phenol red to form bromophenol blue.

The sterilization monitor can be used to monitor sterilization processes that use a peracid vapor. The peracid may be any of the conventional peracids known to be useful as sterilants. The peracids may contain, for example, between one and eight carbon atoms, may be saturated or unsaturated, may be halogenated, and may be non-aromatic or aromatic. Examples include performic acid, peracetic acid, perpropinoic acid, perbutanoic acid, etc.

The sterilization process may include, for example, exposure to an atmosphere containing at least 5% peracetic acid vapor for at least 10 minutes or 15 minutes. The sterilization process may be conducted at elevated (greater than 40° C.) temperatures. The sterilization process may include use of other sterilants (e.g., hydrogen peroxide) in addition to a peracid, or may include a plasma step that may, for example, involve a peracid. Of course, the sterilization process may not include a plasma step. Sterilization processes that include use of peracids are described, for example, in U.S. Pat. No. 5,084,239 and U.S. Pat. No. 5,244,629.

Examples of Sterilization Monitors for Liquid Phase Sterilization Processes

A preferred sterilization monitor for liquid phase sterilization processes also includes a monitor composition and a substrate.

The monitor composition undergoes a distinct color change when exposed to peracid liquid, e.g., peracetic acid. For example, the monitoring composition, carried on the substrate, may exhibit the distinct color change within a certain period of time (e.g., 1 second, 5 minutes, 15 minutes, or 2 hours) of exposure to a solution containing at least 1000 ppm of peracetic acid at 50° C. The color of the monitoring composition (prior to or after exposure to peracetic acid) preferably does not change or fade if left in a darkened environment, e.g., a drawer. The composition will fade, however, if exposed for an extended time, e.g. a month, to a lighted environment.

A preferred monitoring composition contains a dye, a halogen source, and a buffer.

The dye is susceptible to halogenation in the presence of a halogen source and peracid, and changes color as a result of the halogenation to provide an indication that peracid is present. Once halogenated, depending on the dye, peracid concentration, exposure temperature and exposure time, other reactions may take place which cause the halogenated dye to undergo a distinct color change that provides an indication of the concentration of the peracid in solution. For example, the halogenated dye may undergo further halogenation, or may undergo other chemical reactions, or may be pH sensitive.

Once halogenation and subsequent reactions are complete the color of the dye does not change if left exposed to normal air. As a result, assuming the dye is th, only colorant in the monitoring composition, once halogenation and subsequent reactions of the dye are complete the color of the indicator composition is essentially fixed.

Examples of dyes that may be used include the salt or free acid of phenol red, cresol red, fluorescein, chlorophenol red, m-cresol purple, pyrogallol red, crystal violet lactone, 3,4, 5,6-tetrabromophenol sulfone phthalein, 3',3",5',5"-tetraiodophenol phthalein, 4, 5, 6, 7-tetrachlorofluorescein, basic fuchsin, phenolphthalein, xylene cyanole FF, as well as other triphenylmethyl type dyes, fluorescein type dyes, and phenolphthalein type dyes. Other dyes include resorufin, indigo carmine, thionin, variamine blue, indophenol, neutral red, pararosaniline acetate, erioglaucine, malachite green oxalate, indigo, and bromocresol green.

A monitoring composition containing a bromine source and phenol red, for instance, in the presence-of a solution containing 2000 ppm peracetic acid, will turn from red to blue. In the presence of a solution containing 5000 ppm peracetic acid, the monitoring composition will turn from red to yellow/lime green.

A sufficient quantity of the dye should be included in the monitoring composition to provide the desired color intensity. The quantity of the dye in the composition also will influence the rate at which the composition undergoes the distinct color change. The indicator composition may contain, for example, between 0.0001% and 10%, or between 0.01% and 5.0%, of the dye by weight.

The halogen source is preferably bromide and can be, for example, a halogen salt, such as alkaline earth metal halide salts (e.g., calcium bromide and magnesium bromide) or alkali metal halide salts (e.g., lithium bromide and potassium bromide). The halogen source can also be iodide (e.g, lithium iodide, calcium iodide, and magnesium iodide) or an ionic organic halide (e.g., tetra alkyl ammonium bromide or tetra alkyl ammonium iodide). A sufficient quantity of the halogen source should be included in the monitoring composition to react with a sufficient quantity of the dye to cause the color change at the desired rate. The monitoring composition may contain, for example, between 0.1% and 50%, or 10% and 30%, of the bromine source by weight.

The buffer component of the monitoring composition provides a more definite color change due to dye halogenation both by controlling the pH of the monitoring composition and by making the monitoring composition less sensitive to pH. The buffer, however, may not be necessary for the halogenation of the dye to occur and in some monitoring compositions, the buffer may not be a necessary component of the monitoring composition. One skilled in the art could determine, depending on the dye, if the monitoring composition should include a buffer component.

The buffer, if used, is preferably sodium acetate. Other buffers, e.g., phosphates, citrates and the like, which are known to those skilled in the art can be used. The monitor composition can contain 0.0% to 80% sodium acetate by weight. Preferably, the monitor composition when dissolved in a suitable solvent, e.g., water, contains enough sodium acetate to produce a one molar solution (8.2 grams in 100 grams of water).

The monitor composition optionally may include other ingredients such as colorants that do not change color during the sterilization process, resins that perform several functions (e.g., binding, providing water resistance or solvent dispersibility), or other common ink components and opacifying agents.

The components of the peracid monitor composition can be adjusted, e.g., increasing or decreasing their concentration in the composition, to monitor a peracetic acid liquid phase sterilization process to determine whether the sterilization process meets pre-determined parameters, e.g., exposure temperature, exposure peracid concentration, and exposure time. The pre-determined parameters include an exposure temperature between 0° C. and 100° C., an exposure peracid concentration between 100 ppm and 10000 ppm, and an exposure time between 1 second and 30 minutes. Preferably, the exposure temperature is between 20° C. and 60° C., the exposure peracetic acid concentration is between 1000 ppm and 5000 ppm, and the exposure time is between 1 second and 15 minutes. For example, the concentration of dye in the monitoring composition can be decreased to monitor a sterilization process with a decreased exposure time.

Prior to application to the substrate, the monitor composition is dissolved/dispersed in a suitable solvent (e.g., water). Generally, 10 parts of solvent to one part of the monitoring composition is used.

The substrate includes those described previously. Preferably the substrate is a filter paper, SS-410, supplied by Schleicher & Schuell located in New Hampshire.

The monitor composition may be applied to the substrate by conventional techniques, e.g., dip, draw down, or air knife coating, and the like.

When a monitor composition containing, for example, potassium bromide is contacted with a solution containing peracetic acid, bromine is generated. The bromine contacts the dye causing a first color change. The halogenated dye may undergo additional reactions depending on the dye, peracetic acid concentration, exposure temperature, and exposure time, which causes the monitoring composition to undergo a second color change that, e.g., may provide an indication of the concentration of the peracetic acid present in the solution.

Example 3 is an example of a liquid phase monitor composition. Example 4 is an example of a liquid phase sterilization monitor.

EXAMPLE 3

A monitor composition (in solvent) was prepared that contained the following ingredients:

| Ingredient | Quantity | Supplier |
| --- | --- | --- |
| Phenol Red, Sodium Salt | 220 mg | Aldrich |
| Potassium Bromide | 2.0 Grams | Aldrich |
| Sodium Acetate | 8.2 Grams | Aldrich |
| Distilled Water | 100.0 Grams | |

The monitoring solution was tested by the following procedure. 5.0 ml of the above solution was added to 5.0 ml of each of the following solutions (concentrations are approximate):

| | Peracetic Acid | Acetic Acid | Hydrogen Peroxide |
| --- | --- | --- | --- |
| (a) | 0000 ppm | (distilled water control) | |
| (b) | 1000 ppm | 1300 ppm | 200 ppm |
| (c) | 1500 ppm | 2000 ppm | 300 ppm |
| (d) | 2000 ppm | 2600 ppm | 400 ppm |
| (e) | 2500 ppm | 3300 ppm | 500 ppm |
| (f) | 3000 ppm | 4000 ppm | 560 ppm |
| (g) | 3500 ppm | 4600 ppm | 660 ppm |
| (h) | 4000 ppm | 5300 ppm | 750 ppm |
| (i) | 10000 ppm | 13300 ppm | 1900 ppm |

The initial color of the monitor solution is red. After addition of the solutions listed above, the color changes as follows:

| | Peracetic Acid | Color Change |
| --- | --- | --- |
| (a) | 0000 ppm | Red |
| (b) | 1000 ppm | Purple |
| (c) | 1500 ppm | Deep Blue |
| (d) | 2000 ppm | Deep Blue |
| (e) | 2500 ppm | Deep Blue |
| (f) | 3000 ppm | Yellow/Lime Green |
| (g) | 3500 ppm | Yellow/Lime Green |
| (h) | 4000 ppm | Yellow/Lime Green |
| (i) | 10000 ppm | Yellow/Lime Green |

The quantities of acetic acid and hydrogen peroxide reflect dilutions of the original peracetic acid solution with water. The composition worked best when the concentration of hydrogen peroxide in the solution is less than about 20% of the concentration of peracetic acid in the solution.

EXAMPLE 4

A monitor composition (in solvent) was prepared that contained the following ingredients:

| Ingredient | Quantity | Supplier |
| --- | --- | --- |
| Phenol Red, Sodium Salt | 110 mg | Aldrich |
| Potassium Bromide | 2.0 Grams | Aldrich |
| Sodium Acetate | 8.2 Grams | Aldrich |
| Distilled Water | 100.0 Grams | |

The composition was prepared and tested according to the following procedure. The monitoring composition is measured and mixed in a acceptable vessel, e.g., beaker. The monitor solution is coated onto SS-410 paper in the following manner. The SS-410 paper is mounted into a plastic handle and dipped into the monitor solution for 30 seconds. The SS-410 paper is removed and the excess solution is allowed to drain off of the paper. The coated SS-410 paper is then dried in an oven for 30 minutes at 60° C. The dried strips are removed and left at room temperature and with normal exposure to light for 24 hours. One coated substrate is dipped for one second into the following solutions:

|     | Peracetic Acid | Acetic Acid | Hydrogen Peroxide |
| --- | --- | --- | --- |
| (a) | 0000 ppm | (distilled water control) | |
| (b) | 1000 ppm | 1300 ppm | 200 ppm |
| (c) | 1500 ppm | 2000 ppm | 300 ppm |
| (d) | 2000 ppm | 2600 ppm | 400 ppm |
| (e) | 2100 ppm | 2800 ppm | 400 ppm |
| (f) | 2200 ppm | 2900 ppm | 400 ppm |
| (g) | 2300 ppm | 3100 ppm | 400 ppm |
| (h) | 2400 ppm | 3200 ppm | 500 ppm |
| (i) | 2500 ppm | 3300 ppm | 500 ppm |
| (j) | 2600 ppm | 3500 ppm | 500 ppm |
| (k) | 2700 ppm | 3600 ppm | 500 ppm |
| (l) | 2800 ppm | 3700 ppm | 500 ppm |
| (m) | 2900 ppm | 3900 ppm | 500 ppm |
| (n) | 3000 ppm | 4000 ppm | 560 ppm |
| (o) | 3500 ppm | 4600 ppm | 660 ppm |
| (p) | 4000 ppm | 5300 ppm | 750 ppm |
| (q) | 10000 ppm | 13300 ppm | 1900 ppm |

Once removed, the excess solution is allowed to drain and the substrate is air dried. The color of the monitor composition on the dried substrate changes (initially) from red to deep blue at 1000 ppm of peracetic acid. The color change remains deep blue until the concentration of peracetic acid reaches about 2300 ppm at which point the color change begins to show traces of green. The color change is completely green with peracetic acid concentrations from 2600 to 2800 ppm. The color change remains green with peracetic acid concentrations greater than 2800 ppm up to at least 10,000 ppm.

The monitor compositions can be used to monitor sterilization processes that use liquid peracid solutions. The sterilization process can include, for example, exposure to a peracetic acid solution containing at least 1000 ppm (preferably 2000 ppm) peracetic acid liquid for at least 10 minutes or 15 minutes. Sterilization processes using peracetic acid solutions are described, for example, in U.S. Pat. No. 4,892,706, which is incorporated by reference herein. The sterilization process can be conducted at elevated (greater than 40° C.) temperatures. The sterilant solution used in the sterilization process can include, in addition to a peracid liquid, other liquid sterilants, e.g., hydrogen peroxide.

The liquid peracid may be any of the conventional peracids known to be useful as sterilants. The peracids may contain, for example, between one and eight carbon atoms, may be saturated or unsaturated, may be halogenated, and may be non-aromatic or aromatic. Examples include performic acid, peracetic acid, perpropinoic acid, perbutanoic acid, etc.

Examples of Sterilization Monitoring Devices

Sterilization monitors used to monitor vapor phase and liquid phase sterilization processes may be attached as a label to the item to be sterilized, used as masking tape to seal a package containing the item to be sterilized, or simply included in the sterilization chamber along with the item(s) to be sterilized. The sterilization process may involve, for example, sterilization of medical instruments (e.g., fiber optic devices, endoscopic equipment), gloves, linen, parenteral drugs, etc.

Sterilization monitors also can be included in a peracid vapor-permeable package, with or without the item(s) to be sterilized, creating a sterilization monitoring device.

A preferred sterilization monitoring device includes a housing and a monitor composition carried on a substrate.

Referring to the figure, a sterilization monitoring device 10 includes a substrate 50 containing a monitor composition 51, a housing 20 having a durable transparent top 30, e.g., MYLAR™ polyester film coated with SURLYN™, polyvinylchloride (PVC) and glycol modified polyethylene terephthalate (PETG), defining a vapor head space 60, and a microporous bottom 40, e.g., GORE-TEXT™, TYVEK™ and COTRANT™. Substrate 50 includes a laminated side 52, e.g. MYLAR™ polyester film coated with SURLYN™, which is mounted, e.g., taped, to microporous bottom 40. The monitor composition includes the components described previously. Durable transparent top 30 is sealed, e.g., heat sealed or glued, to microporous bottom 40 to enclose substrate 50 within vapor head space 60.

During a sterilization process, sterilization monitoring device 10 is submerged in a sterilant solution containing a peracid. The peracid vapor penetrates microporous bottom 40, enters vapor head space 60, and contacts monitor composition 51 of substrate 50 causing a color change of monitor composition 51, observable through transparent top 30.

The preferred sterilization monitoring device includes a laminated substrate chosen to inhibit peracid vapor from directly penetrating the microporous barrier and contacting the underside of the substrate. Direct penetration of the peracid vapor to the underside of the substrate may cause the monitor composition to undergo a distinct color change generally irrespective of peracid concentration, exposure time or sterilant temperature. The lamination provides a controlled color change by forcing the peracid vapor to first contact the monitor composition on the perimeter of the substrate causing a color change of the monitor composition. Then, as the peracid vapor fills the vapor head space, the peracid vapor contacts the monitor composition in the center of the substrate causing a color change of the monitor composition. The location of color change of the monitor composition is used to monitor sterilization processes. For example, if the center of the substrate does not display a color change, the sterilization process did not meet predetermined parameters. The predetermined parameters, described above, include exposure temperature, exposure peracid concentration, and exposure time.

The vapor head space of the sterilization monitoring device allows the peracid vapor to equilibrate and to accurately monitor peracid sterilization processes for a given set of pre-determined parameters.

The preferred sterilization monitoring device includes a PVC or PETG top, a TYVEK™ microporous bottom, and a ⅝" square piece of SS-410 filter paper laminated on one side. Preferably, the top defines a vapor head space of ⅜" to ⅛" above and to the sides of the substrate and is sealed to the tyvek microporous bottom.

Preferably the top is heat sealed to the bottom reducing the addition of further chemicals that may be added to the sterilization chamber by using a glue or epoxy. However, a properly chosen glue, e.g., Loctite 411 instant adhesive, can also be used.

A sterilization monitoring device including a monitor composition having a starting monitor composition color is immersed in a peracid solution of a sterilization process. As peracid vapor penetrates the vapor permeable bottom and fills the vapor head space, it contacts the monitor composition causing a color change of the monitor composition. The color change of the monitor composition proceeds from the perimeter of the device inward.

For example, a sterilization monitoring device including a monitor composition having phenol red and potassium bromide is immersed into a peracetic acid solution of a sterilization process. The starting color of the monitor composition is red. As peracetic acid vapor penetrates the vapor permeable bottom, a first dark blue color change of the monitor composition appears on the perimeter of the substrate. As exposure to peracetic acid continues, the dark blue color change moves inward toward the center of the coated substrate followed by a second color change, yellow-green (lime), which also begins at the perimeter of the substrate and moves inward. If the predetermined parameters of the sterilization process have beer met (e.g. 12 minutes, 2000 ppm peracetic acid, 54° C.), the entire monitor composition turns completely lime. If the pre-determined parameters have not been met, then a dark blue may remain in the center of the substrate surrounded by lime.

The sterilization monitoring device may also include an identification marker, e.g., a writable portion or tag, used to date and label the sterilization monitoring device, or that can be used as a record. The sterilization monitoring device may also include a monitor composition including a buffer, halogen source, and colorant which replicates and/or is substantially parallel to and/or substantially mimics the response of biological indicators, e.g., Bacillus Stearothermophulus, to a sterilization process.

Many of the materials used to construct the sterilization monitoring device are easily obtained. TYVEK™ 1025D is a spunbonded olefin available from the E.I. Du Pont De Nemours and Company, located in Wilmington, Del. MYLAR™ is a polyester film coated with SURLYN™, a ethylene/methacrylic acid ionomer resin, supplied from the Donahue-Corry Associates, located in Dover, Mass. (MYLAR™ and SURLYN™ are trademarks of E.I. Du Pont De Nemours and Company). COTRAN™ is a microporous polyethylene film available from the Minnesota Mining and Manufacturing Company, located in St. Paul, Minn. GORE-TEX™ is a fabric available from W. L. Gore and associates, Inc., located in Newark, Del.

Example 5 and 6 are examples of sterilization monitoring devices.

EXAMPLE 5

The same monitor composition as used in Example 3 is coated onto ⅝" square 0.01" thick pieces of SS-410 filter paper having one laminated side. The SS-410 paper is mounted into a plastic handle and dipped into the monitor solution for 30 seconds. The SS-410 paper is removed and the excess solution is allowed to drain off of the paper. The coated SS-410 paper is then dried in an oven for 30 minutes at 60° C. The dried strips are removed and left at room temperature and with normal exposure to light for 24 hours.

The laminated side of the coated paper is taped, e.g., double sided, to the center of a 2" square 0.01" thick piece of TYVEK™ type 10 1025 D spunbonded olefin, available from E.I. Du Pont De Nemours and Company, located in Wilmington, Del. The substrate is enclosed within the sterilization monitoring device by the following manner. A 2" square 0.00" piece of PVC, PJN-9708623, supplied by Perfecseal located in Minnesota, having a central 1" square ⅜" deep vapor head space is glued, using Loctite 411 instant adhesive, to the TYVEK™.

Seven devices made by the procedure described above were placed in a 2 liter beaker containing variable concentrations of peracetic acid for various times and temperatures. For 12 minutes at 54° C., submerged in 2000 ppm peracetic acid, 3 devices in tandem showed the following results:

| Device | % Change to Final Color (Lime) |
|--------|--------------------------------|
| a      | 100%                           |
| b      | 95–100%                        |
| c      | 90–100%                        |

For 12 minutes in 1500 ppm peracetic acid at 54° C., two devices showed the following results.

| Device | % Change to Final Color (Lime) |
|--------|--------------------------------|
| d      | 50%                            |
| e      | 50–60%                         |

For 12 minutes in 2500 ppm peracetic acid at 54° C., two devices showed the following results.

| Device | % Change to Final Color (Lime) |
|--------|--------------------------------|
| f      | 100%                           |
| g      | 100%                           |

Devices b and c were left for longer times at 2000 ppm peracetic acid and 54° C. and both turned 100% lime. Exposing the devices to shorter times or lower ppm peracetic acid produce substantially less lime. Higher temperatures show more lime as does higher concentration of peracetic acid. As a result, the device may be used to monitor the effects of pre-determined parameters, e.g., peracetic acid concentration, time of exposure, and temperature of sterilant solution.

EXAMPLE 6

The same monitor composition as used in Example 3 is prepared. The pH of the monitor composition is measured as 7.5. The monitor composition having is then coated onto two pieces of SS-410 filter paper and each substrate is mounted in a sterilization monitoring device as described in Example 5.

A second monitor composition as used in Example 3 is prepared. The pH of the monitor composition is measured as 7.5. A 0.1 N NaOH solution is added to the composition raising the pH to 10. The monitor composition is then coated onto two pieces of SS-410 filter paper and each substrate is mounted in a sterilization monitoring device as described in Example 5.

At 54° C., submerged in 2000 ppm peracetic acid, one device made with a substrate having a monitor composition with a pH of 7.5, in tandem with one device made with a substrate having a monitoring composition with a pH of 10, showed the following results:

| Device | % Change to Final Color (Lime) |
|---|---|
| pH 7.5 | 100% with an 11 minute exposure |
| pH 10 | 100% with an 12 minute exposure |

For 12 minutes at 54° C., submerged in 2000 ppm peracetic acid, 2 other devices in tandem showed the following results:

| Device | % Change to Final Color (Lime) |
|---|---|
| pH 7.5 | 95% |
| pH 10 | 100% |

In other embodiments, a sterilization monitoring device includes a monitor composition and a multiple housing, i.e., one housing, as described above, enclosing another. The monitor composition is preferably a liquid, such as the monitor composition from Example 3.

Other embodiments are within the claims.

What is claimed is:

1. A method of monitoring a peracid liquid phase sterilization process, comprising
   exposing a monitoring composition including a colorant and a halogen source to a peracid from a sterilization solution during a peracid liquid phase sterilization process, wherein said colorant is susceptible to halogenation by said halogen source and the composition will change to a particular color if the sterilization process meets pre-determine sterilization parameters and detecting a color change of said monitor composition.

2. The method of claim 1, wherein the predetermined sterilization parameters include exposure time.

3. The method of claim 2, wherein the exposure time is at least 1 minute.

4. The method of claim 1, wherein the predetermined sterilization parameters include exposure temperature.

5. The method of claim 4, wherein the exposure temperature is at least 25° C.

6. The method of claim 1, wherein the predetermined sterilization parameters include concentration of a peracid in the sterilization solution.

7. The method of claim 6, wherein the exposure concentration of a peracid from a sterilization solution is at least 1000 ppm.

8. The method of claim 1, wherein the predetermined sterilization parameters include exposure time and exposure concentration of a peracid from a sterilization solution.

9. The method of claim 1, wherein the predetermined sterilization parameters include exposure temperature and exposure concentration of a peracid from a sterilization solution.

10. The method of claim 1, wherein the predetermined sterilization parameters include exposure time, exposure temperature and exposure concentration of a peracid from a sterilization solution.

11. The method of claim 10, wherein the exposure time is at least 1 minute, the exposure temperature is at least 25° C., and the exposure concentration of a peracid from a sterilization solution is at least 1000 ppm.

12. The method of claim 11, wherein said halogenated colorant is susceptible to additional reactions which cause the monitoring composition to undergo a distinct color change that provides an indication if the sterilization process meets said pre-determined sterilization parameters.

13. The method of claim 11, wherein said halogen comprises bromine or iodine.

14. The method of claim 11, wherein the concentration of a peracid from a sterilization solution is at least 1000 ppm.

15. The method of claim 11, wherein said colorant comprises phenol red.

16. The method of claim 11, wherein said monitor composition is enclosed within a housing including a vapor permeable barrier and wherein peracid vapor passes through the barrier to contact the monitor composition and cause the halogenation.

17. A method of determining whether a liquid solution including peracetic acid has a concentration at about 2500 ppm, comprising
   exposing a monitor composition, including a colorant and a halogen source, wherein said colorant is susceptible to halogenation by said halogen source, to a liquid sterilization solution including peracetic acid under conditions that will cause the composition undergo a color change at about 2500 ppm of peracetic acid and detecting a color change of said monitor composition.

18. The method of claim 17, wherein the halogen source halogenates the colorant to cause a color change in the monitor composition that provides an indication of the concentration of the peracetic acid in the solution.

* * * * *

UNITED STATES PATENT AND TRADEMARK OFFICE
CERTIFICATE OF CORRECTION

PATENT NO.   : 6,440,744 B1  
DATED        : August 27, 2002  
INVENTOR(S)  : Ignacio, Ramon T.

It is certified that error appears in the above-identified patent and that said Letters Patent is hereby corrected as shown below:

<u>Title page</u>,  
Item [54], Title, "STERILIZATION MONITORING SYSTEM" should read  
-- STERILIZATION MONITORS --.

<u>Column 1</u>,  
Line 34, "professionals" should read -- professional --.

<u>Column 5</u>,  
Line 19, delete "in".

<u>Column 6</u>,  
Line 26, "th," should read -- the --.

<u>Column 10</u>,  
Line 9, "GORE-TEXT$^{TM}$" should read -- GORE-TEX --.  
Line 10, "COTRANT$^{TM}$." should read -- COTRAN$^{TM}$. --

<u>Column 11</u>,  
Line 13, "beer" should read -- been --.  
Line 61, "0.00"" should read -- 0.01" --.

<u>Column 14</u>,  
Lines 17, 22, 24, 26 and 28, "11" should read -- 1 --.

Signed and Sealed this

Thirteenth Day of April, 2004

JON W. DUDAS  
*Acting Director of the United States Patent and Trademark Office*